United States Patent [19]

Noyes

[11] 4,069,955

[45] Jan. 24, 1978

[54] DISPOSABLE CARRIER FOR CARDIAC TELEMONITOR TRANSMITTER

[75] Inventor: Richard S. Noyes, Convent Station, N.J.

[73] Assignee: Laser Systems & Electronics, Inc., Tullahoma, Tenn.

[21] Appl. No.: 710,523

[22] Filed: Aug. 2, 1976

[51] Int. Cl.² ........................................... A45C 11/00
[52] U.S. Cl. .................................... 224/5 H; 24/3 B; 128/2.06 F
[58] Field of Search ..................... 224/5 R, 5 BC, 5 H, 224/5 L, 5 V, 5 W, 5 Y, 26 R, 26 K, 26 J, 28 R, 28 A, 28 B; 248/102; 128/2.06 A, 2.06 F, 351, 419 PS, DIG. 4; 24/3 A, 3 B, 3 F; 206/363, 364, 438

[56] References Cited

U.S. PATENT DOCUMENTS

| 651,647 | 6/1900 | Bird | 248/102 |
|---|---|---|---|
| 931,627 | 8/1909 | Lazardvich-Hrebelianovich | 224/28 B |
| 2,372,971 | 4/1945 | Moore | 224/5 H |
| 2,676,738 | 4/1954 | Herrick | 224/5 H |
| 2,688,752 | 9/1954 | Sbarra et al. | 224/5 H X |
| 2,710,639 | 6/1955 | Farls | 224/26 R X |
| 3,942,535 | 3/1976 | Schulman | 128/419 PS |

FOREIGN PATENT DOCUMENTS

| 1,168,796 | 3/1957 | France | 224/26 R |
|---|---|---|---|
| 2,014,315 | 10/1971 | Germany | 224/28 B |

OTHER PUBLICATIONS

Aerospace Medicine; Richardson, "Some New Electrode Techniques for Long-Term Physiologic Monitoring"; July 1968; pp. 745–750.

Primary Examiner—Lawrence J. Oresky
Assistant Examiner—Winston H. Douglas
Attorney, Agent, or Firm—Lionel N. White

[57] ABSTRACT

A carrying pouch for a cardiac telemonitor transmitter unit is made of a soft absorbent sheet material, such as an open-pored non-woven fabric, and includes a pair of ribbon tie strips by which the carrier may be affixed about the neck and chest of a cardiac patient to secure the transmitter against artifact generating movement. A seam vent in the pouch permits ready access to the contact lead coupling means on the transmitter.

3 Claims, 4 Drawing Figures

DISPOSABLE CARRIER FOR CARDIAC TELEMONITOR TRANSMITTER

BACKGROUND

During the recuperation of cardiac patients resident in hospital facilities, extensive use is made of the telemetric monitoring system which provides a constant indication to hospital personnel of the cardiac condition of the patient, particularly ECG data and heartbeat rate, during the patient's ambulatory period. Such telemonitoring systems comprise a cigarette package-sized radio transmitter carried by the patient and to which are attached leads from ECG electrode contacts adhered to the skin of the patient at appropriate thoracic locations.

It has previously been common practice to attach the telemonitor transmitter unit to the patient's body by means of adhesive tape or to insert the transmitter unit into a convenient pocket in the patient's bedjacket or bathrobe. The well-known discomfort associated with the removal of broad adhesive strips from one's person and the additional discomfort and dermal irritation resulting from the entrapment of perspiration beneath the closely held transmitter and such adhesive strips have generally rendered this practice undesirable.

While the use of apparel pockets as carrying means for transmitters is somewhat more preferable from the point of view of the patient's personal comfort, the unbound freedom of movement of the transmitter with the activity of the patient tends toward the generation of false cardiac signals, or artifacts, which inhibit the careful monitoring of the patient's condition. A further problem associated with the practice of utilizing wearing apparel as a carrying means for telemonitoring transmitters is occasioned by the not too different emergency condition into which a cardiac patient may lapse and which results in the need for immediate disrobement of the patient. As a result of such emergency activities, the apparel containing the telemonitor transmitter is often discarded in such a manner as to result in permanent damage to the transmitter.

SUMMARY OF THE INVENTION

As a means of avoiding the personal discomfort associated with the use of adhesive tape while nonetheless effecting close containment of the transmitter unit upon the patient during ambulatory ECG monitoring, there is provided, in accordance with the present invention, a carrier pouch which is not only readily and comfortably affixed to the patient, but is also sufficiently inexpensive in its material and structure to allow disposal after a reasonable period of service, thereby eliminating a significant cost factor in patient care.

The telemonitoring transmitter carrier of the present invention is fashioned of open-pored material, such as a non-woven fabric of the type commonly employed as household or industrial wiping cloth, and is constructed in the form of a substantially rectangular pouch open at its upper end with a bottom seam vent in the area of one of its lower corners. As will be described in greater detail below, the open vent portion of the lower pouch seam receives the outwardly extending connector terminal of the transmitter and provides access to that junction for the coupling of the patient electrode leads.

The pouch structure further includes two pairs of slits in the fabric along the edges of the generally rectangular shape of the pouch. Each of the pairs of such slits accomodates the insertion of one of a pair of textile ribbon strips by which the transmitter pouch carrier is tied about the body of the cardiac patient. It is preferred in the embodiment of this invention that the slit pair and ribbon more closely disposed to the lower, or vented, seam edge of the pouch be situated so as to overlie substantially the central region of a telemonitoring transmitter unit contained within the pouch carrier. By such an arrangement that ribbon tied about the patient's body firmly contains the transmitter against independent movement thereby preventing the jarring which causes the generation of ECG artifacts. The second of the slit pairs and associated ribbon material are disposed at any practical location near the open mouth end of the carrier pouch. That ribbon tied about the patient not only adds support to the transmitter carrier pouch, but also effects a pursed closure of the pouch to further restrict extraneous motion of the transmitter.

DRAWINGS

DESCRIPTION

Figure 1:
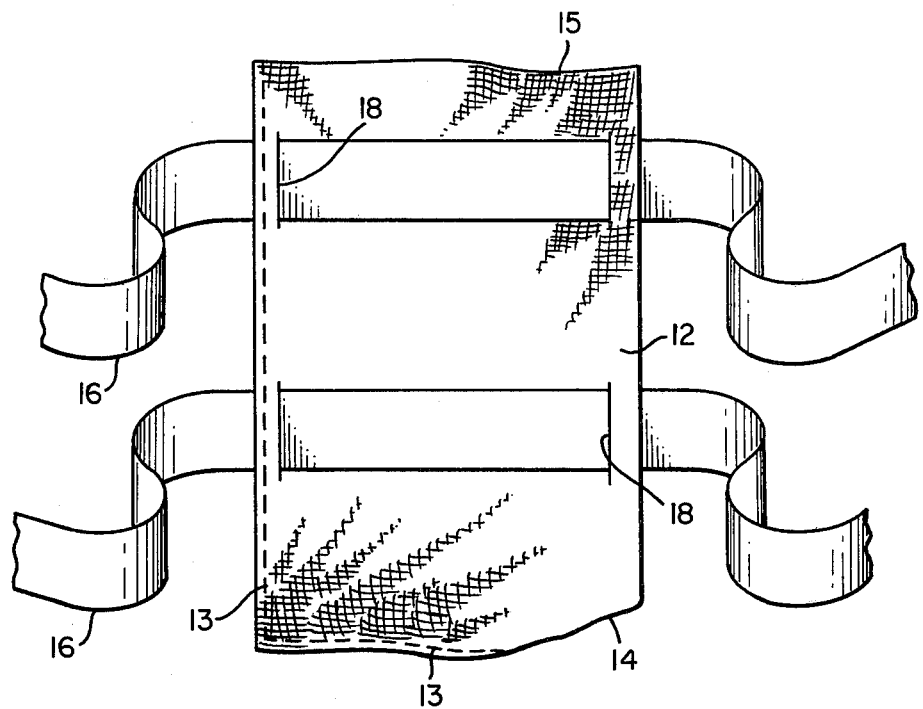
FIG. 1 shows the arrangement of a carrier pouch and ties according to the present invention.

With reference to FIG. 1 it will be seen that the telemonitoring transmitter carrying pouch of the present invention comprises a body 12 of an open-pored absorbent sheet material, such as a non-woven fabric, and a pair of textile ribbon strips 16 which pass through slits 18 in the pouch body and overlie substantially the whole of one side of the rectangular form of body 12.

Body 12 of the transmitter carrier may be formed of a single sheet of nonwoven fabric in the manner shown in FIG. 1 where such a sheet is folded double and stitched at 13 along the open vertical longitudinal and bottom lateral edges to form the pouch open initially only at the top lateral edge 15. A bias cut through the pouch at one lower corner forms a vent opening as at 14 through which the electrode lead connector junction of the transmitter becomes accessible as will later be shown. In an alternative embodiment of the invention, a suitable activated or fluid adhesive may be substituted for the closure stitching shown at 13. As a further alternative embodiment, side stitching may be eliminated through the use of tubular fabric stock material thus requiring closure only along one open end to form the bottom of the pouch which may then be vented as at 14.

Slits 18 may be readily cut through the double layer of fabric while the pouch body 12 is in a closed disposition to thus provide for the insertion of textile ribbon strips 16. The pair of slits 18 disposed more closely to the closed and vented end of the pouch body 12 are preferably located to overlie substantially the central lateral region of the body of the telemonitoring transmitter contained within the carrier pouch. It has been found that locating this lower pair of slits 18 about 60 mm. from the vented end of the carrier pouch will serve effectively to thus embrace most transmitters in present use. The upper ribbon slits are disposed at about 140 mm. from the vented end of the carrier pouch, according to present typical transmitter size, and will normally be within about 40 mm. of the open end 15 of the pouch in order to effect a pursed closure in final application. Ribbons 16 threaded through slits 18 in the body of the carrier pouch are selected to be of sufficient length to encompass the chest of the cardiac patient and may average about 1.5 meters in length.

Figure 2:
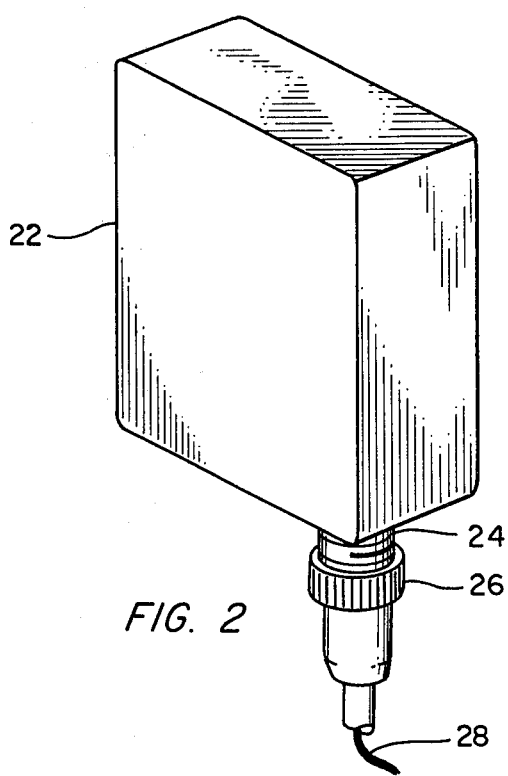
FIG. 2 shows a typical cardiac telemonitor transmitter unit.

A typical telemonitoring system transmitter unit is shown in FIG. 2 and comprises a body 22 within which are contained a power battery and signal-transmitting electronics. An extending neck portion 24 is provided to receive coupling element 26 by which electrode leads 28 are brought into circuit with the transmitting electronics. It is to accomodate this connector neck 24 that vent provision 14 is made in the body 12 of the carrier pouch.

Figure 3:
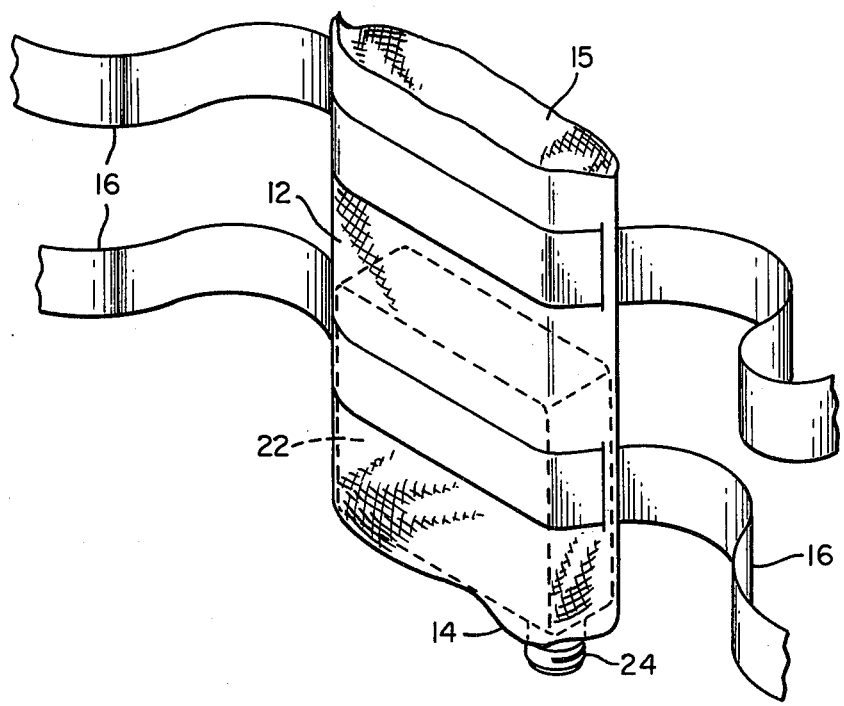
FIG. 3 shows a transmitter unit located within a carrier pouch of the present invention.

FIG. 3 depicts a telemonitoring transmitter positioned within pouch body 12 ready for affixing to a patient. Connector neck 24 of the transmitter unit may be seen protruding from access vent 14 ready for attachment of connector 26 and leads 28 after the electrodes have been appropriately attached to the patient.

Figure 4:
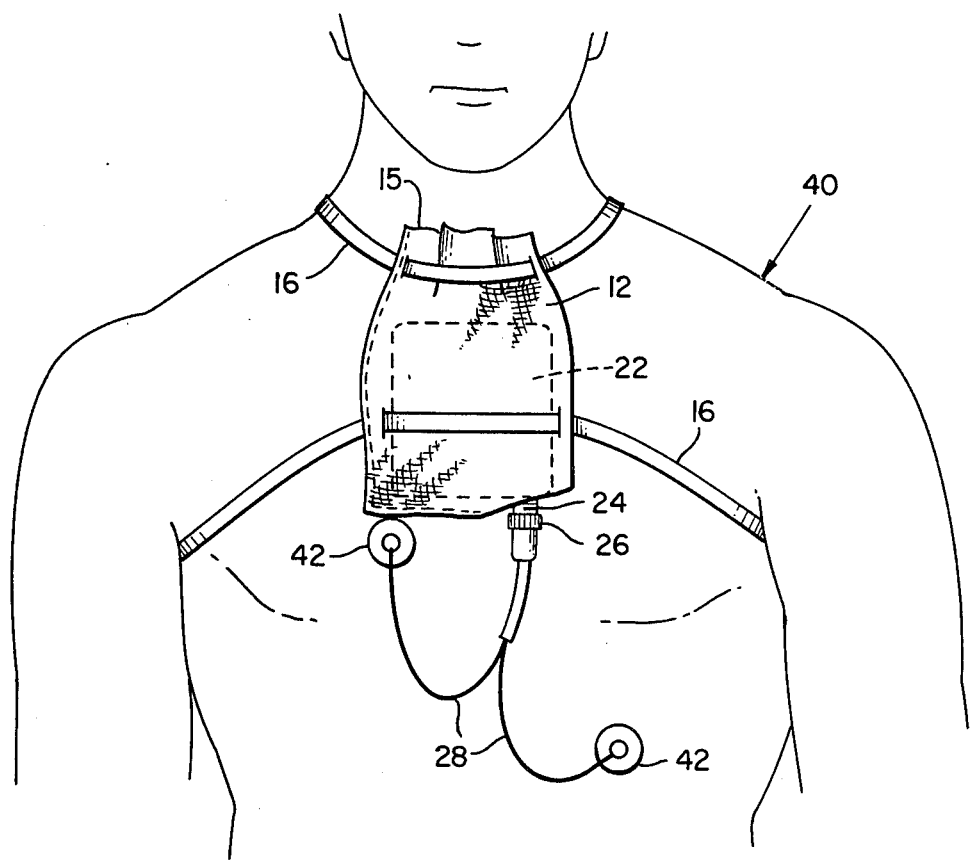
FIG. 4 shows a typical manner of affixing the transmitter-containing carrier of the present invention about the person of a cardiac patient.

In FIG. 4 is shown a typical manner of attaching a telemonitoring transmitter unit to an ambulatory cardiac patient by means of the carrier pouch of the present invention. After insertion of the transmitter unit 22 to be loosely contained within the body 12 of the carrier pouch, upper ribbon 16 is comfortably tied about the neck of patient 40 in order that pouch 12 may be suspended at a convenient elevation upon the body of the patient. The weight of transmitter 22 causes the pursed closure of the open entry end 15 of pouch 12 to protect against accidental removal of the transmitter unit and to assist in containing the unit against vibration and movement. Lower ribbon 16 overlying the body of transmitter 22 is then tied about the chest and back of patient 40 to comfortably yet firmly affix the transmitter to the patient 40 and prevent artifact-generating vibrations of transmitter 22 during movement of the patient.

ECG electrodes 42 may thereafter be affixed to the patient 40 as prescribed by the physician and electrode leads 28 attached to transmitter 22 by means of coupler 26 and handily accessible connector neck 24 protruding from the access vent. While the carrier pouch and transmitter have been depicted as centrally situated upon the sternal region of patient 40, it should be readily apparent that the configuration of the carrier of the present invention provides for locating the transmitter unit wherever desired upon the body of the patient to more closely accommodate the location of electrodes 42. Such flexibility in the positioning of the telemonitoring transmitter in close association with the region of electrode attachment allows the use of shorter electrode leads 28, thus further ensuring true ECG data signals.

What is claimed is:

1. A carrier for a cardiac telemonitoring transmitter which comprises:
   a. a substantially rectangular envelope of open-pored fabric, said envelope being open across a first lateral edge to provide full access to the interior thereof;
   b. said envelope being normally closed along the three remaining edges thereof but for a vent opening at one end of the second lateral edge providing limited access to the interior thereof thereby to accommodate an outwardly extending connector terminal of said transmitter;
   c. at least two pairs of slits through said envelope, the slits comprising each such pair being disposed substantially equidistant from a lateral edge of said envelope with each one of said slits of each pair being closely adjacent and substantially parallel to a different one of the respective longitudinal edges of said envelope; and
   d. a plurality of ribbons of which each is threaded through a pair of said at least two pairs of slits to thereby overlie substantially the whole lateral width of said envelope, said plurality of ribbons being adapted to be affixed about the body of a cardiac patient.

2. A carrier according to claim 1 wherein the slits comprising the first of said at least two pairs of slits are disposed at a distance from said second lateral edge substantially equal to one-half the longitudinal dimension of the transmitter to be contained within said carrier.

3. A carrier according to claim 2 wherein the slits comprising another of said at least two pairs of slits are disposed at a distance from said second lateral edge which is in excess of twice the distance between said second lateral edge and said first pair of slits.

* * * * *